(12) United States Patent
Liu et al.

(10) Patent No.: US 11,149,335 B2
(45) Date of Patent: Oct. 19, 2021

(54) METHOD FOR DESIGNING MULTI-COMPONENT HIGH-STRENGTH TITANIUM ALLOY

(71) Applicant: Central South University, Hunan (CN)

(72) Inventors: Libin Liu, Hunan (CN); Di Wu, Hunan (CN); Ligang Zhang, Hunan (CN); Zhenyu Wang, Hunan (CN); Jinwen Sheng, Hunan (CN)

(73) Assignee: Central South University, Changsha (CN)

( * ) Notice: Subject to any disclaimer, the term of this patent is extended or adjusted under 35 U.S.C. 154(b) by 334 days.

(21) Appl. No.: 16/352,924

(22) Filed: Mar. 14, 2019

(65) Prior Publication Data
US 2019/0284672 A1  Sep. 19, 2019

(30) Foreign Application Priority Data
Mar. 14, 2018  (CN) .......................... 201810210372.5

(51) Int. Cl.
*C22F 1/18* (2006.01)
*G16C 20/10* (2019.01)
*C22C 1/02* (2006.01)
*C22C 14/00* (2006.01)

(52) U.S. Cl.
CPC ............... *C22F 1/183* (2013.01); *C22C 1/02* (2013.01); *C22C 14/00* (2013.01); *G16C 20/10* (2019.02)

(58) Field of Classification Search
None
See application file for complete search history.

(56) References Cited

PUBLICATIONS

X.D. Zhang, L.B. Liu, J.-C. Zhao, J.L. Wang, F. Zheng, Z.P. Jin, High-efficiency combinatorial approach as an effective tool for accelerating metallic biomaterials research and discovery, Materials Science and Engineering: C, vol. 39, 2014, pp. 273-280 (Year: 2014).*

J.-C. Zhao, Xuan Zheng, David G. Cahill, High-throughput diffusion multiples, Materials Today, vol. 8, Issue 10, 2005, pp. 28-37, (Year: 2005).*

Nag, Soumya, et al. "Non-classical homogeneous precipitation mediated by compositional fluctuations in titanium alloys." Acta Materialia 60.18 (2012): 6247-6256. (Year: 2012).*

* cited by examiner

*Primary Examiner* — Anthony J Zimmer
*Assistant Examiner* — Michael J Kachmarik

(57) ABSTRACT

A method for designing multi-component high-strength titanium alloy, including the following steps: 1. smelting alloy ingots of specific compositions of the research system 2. cutting metal ingots into cubes of desired sizes; 3. preparing multi-component diffusion multiples. 4. performing vacuum-diffusion and annealing on the prepared diffusion multiples. 5. performing solution and aging treatments on the diffusion multiples after vacuum-diffusion and annealing. measuring the composition, microstructure and microhardness of different areas of the diffusion multiples, establishing the database of "composition-microstructure-hardness" correspondence of the titanium alloy. And 8. selecting a titanium alloy meeting design requirements in the titanium alloy database.

7 Claims, 4 Drawing Sheets

METHOD FOR DESIGNING MULTI-COMPONENT HIGH-STRENGTH TITANIUM ALLOY

CROSS-REFERENCE TO RELATED APPLICATIONS

This application claims the benefit of priority from Chinese Patent Application No. 201810210372.5, filed on Mar. 14, 2018. The content of the aforementioned application, including any intervening amendments thereto, is incorporated herein by reference in its entirety.

TECHNICAL FIELD

The present disclosure relates to the technical field of titanium alloy design, in particular to a rapid method for designing multi-component high-strength titanium alloy.

BACKGROUND OF THE PRESENT INVENTION

High-strength titanium alloys generally refer to titanium alloys with a tensile strength exceeding 1100 MPa. Due to their high strength and low density, they are widely used in the aerospace industry as an important structural material. With the development of the aviation industry, titanium alloys are increasingly used on various aircraft, and at the same time, higher demand regarding the performance of titanium alloys is called for. The high-strength titanium alloys Ti-1023 and Ti-5553 widely used in the world have been present in the titanium alloy market for more than 15 years, and their performance cannot meet the performance requirements of the latest generation of aircraft for titanium alloys. However, design ideas for traditional titanium alloys have been difficult to improve the performance of titanium alloys. Further, the long development cycle and high R&D cost of traditional alloy design methods further limit the development of a new generation of high-performance titanium alloys. Therefore, in order to design a new generation of high-performance titanium alloys, it is necessary to establish a new theory about titanium alloy design.

Recently, Yunzhi Wang et al. proposed a pseudo spinodal decomposition mechanism in titanium alloys. The experimental results show that during the aging process of the titanium alloys, when the alloy composition reaches or approaches a certain critical composition, a large amount of nano-sized super fine α phase organization will be formed in a short time. In the subsequent phase field simulation of titanium alloy β→α transformation, it is found that the α phase precipitation efficiency under the pseudo spinodal decomposition mechanism is about 100 times that of the traditional nucleation growth mechanism. Experiments and theories prove that the pseudo spinodal decomposition theory will be an effective means for obtaining ultra-fine α-structure of titanium alloy.

According to the principle of the pseudo spinodal decomposition mechanism, only when the initial composition of the titanium alloy (Calloy) is close to the composition of the β phase (C0) when the Gibbs free energy of the parent phase β phase equals to that of the precipitation phase α, the pseudo spinodal decomposition mechanism will play a role. FIG. 1 shows a schematic diagram of the pseudo spinodal decomposition mechanism[20]. As shown, when Calloy is located near C0, slight fluctuations in the local composition of the alloy (shown by the red arrow) cause the Gibbs free energy of the β and α phases to exhibit a distinct gradient. Among them, when Calloy changes slightly to the left side of C0, the free energy of the β phase increases, and the free energy of the α phase decreases (ie, the energy of the precipitated phase is lower than that of the parent phase), and a relatively significant free energy difference is instantaneously generated between the two phases (shown by the green arrow). This energy difference will provide sufficient driving force for the precipitation of the α phase, so that the alloy will form a large amount of α phase in a short time, that is, the α phase has a high nucleation rate.

In recent years, high-throughput experiments have attracted wide attentions as a new experimental method in the field of material design [8]. Through a series of fast and efficient experimental means and test methods, it is aimed to shorten the experimental period and speed up the research and development. As an important part of the material genetic engineering technology, high-throughput experiments can accelerate material development and achieve pipeline of material development [9]. The high-throughput gradient experimental methods such as diffusion multiple, double-cone strain gradient and temperature gradient to be adopted by the present disclosure will effectively shorten the development cycle of new titanium alloy and improve the experimental efficiency.

In view of the above problems, the present disclosure uses the pseudo spinodal decomposition of titanium alloy as the theoretical basis, and uses CALPHAD phase diagram calculation method combined with diffusion multiple experimental method to design the composition of high-strength titanium alloy. Compared with the previous alloy design method, this method is more targeted under the guidance of the theory, and the experimental method of diffusion multiple is fast, efficient and cost-effective.

SUMMARY OF THE PRESENT INVENTION

The technical problem to be solved by the present disclosure is to overcome the deficiencies of the existing design theories and methods, and to provide a method for designing multi-component high-strength titanium alloy which is fast, efficient, reliable and high in success rate. Through the material design method, the correspondence relationship of the alloy "composition-microstructure-hardness" can be quickly obtained, and thus the alloy design can be carried out in a targeted manner. Compared with the conventional method, this method is more targeted and accurate, and accurately determines the alloy composition. It is fast, efficient, and saves time and effort. This method has utility in design of high-strength titanium alloy composition.

In order to solve the above technical problems, the present disclosure adopts the following technical solutions:

A method for designing a multi-component high-strength titanium alloy, comprising the following steps:

Firstly, using the phase diagram thermodynamic database of titanium alloy, the phase diagram calculation method is used to calculate a variation of the α and β Gibbs free energy of the titanium alloy system with a change of composition of the alloy at a certain temperature, finding the alloy composition range within which the pseudo spinodal decomposition may occur; designing the composition of the alloy used in the diffusion multiple based on the calculation results; and then:

(1) weighing respectively, titanium alloy raw materials—titanium alloy a Ti-b-45Zr, titanium alloy b Ti-b, titanium alloy c Ti-b-20Mo, titanium alloy d Ti-b-20Cr, and titanium alloy e Ti-b-20Fe, smelting to obtain the above five titanium alloy ingots;

(2) cutting respectively, the five titanium alloy ingots obtained in step (1) into cubes, the cubes comprising a titanium alloy a cube, a titanium alloy b cube, a titanium alloy c cube, a titanium alloy d cube, and a titanium alloy e cube;

(3) stacking and fixing the cubes obtained in step (2) sequentially in the order of the titanium alloy a cube, the titanium alloy b cube and the titanium alloy c cube, and sintering them to form a ternary diffusion multiples A;

Stacking and fixing the cubes obtained in step (2) sequentially in the order of the titanium alloy a cube, the titanium alloy b cube and the titanium alloy d cube, and sintering them to form a ternary diffusion multiple B;

(4) stacking and fixing remaining cubes in step (2) as well as the ternary diffusion multiple A and the ternary diffusion multiple B obtained in step (3) in the order of the titanium alloy d cube, the ternary diffusion multiple A, the titanium alloy e cube, the ternary diffusion multiple B and the titanium alloy c cube in a length direction, and sintering them to form a multi-component diffusion multiple; in the multi-component diffusion multiple, the ternary diffusion multiple A comprises titanium alloy a, titanium alloy b and titanium alloy c from bottom to top in a height direction, and the ternary diffusion multiple B comprises titanium alloy a, titanium alloy b and titanium alloy d from bottom to top in a height direction;

(5) performing diffusion annealing treatment on the multi-component diffusion multiple obtained in step (4) to obtain composition gradient;

(6) performing solution treatment and aging treatment on the multi-component diffusion couple obtained in step (5);

(7) dividing sub-regions in a region where the surface titanium alloy b occupies a largest area of the multi-component diffusion couple after the aging treatment, determining composition, structure and hardness of each sub-region, and establishing a titanium alloy database regarding "component-microstructure-hardness" correspondence;

(8) selecting a titanium alloy meeting design requirements in the titanium alloy database obtained in step (7).

Further, a base alloy of the titanium alloy is Ti-b, and the base alloy comprises an α-type titanium alloy and an α-β-type titanium alloy.

Further, the α-type titanium alloy and the α-β-type titanium alloy comprise Ti-6Al-4V, Ti-3Al-2.5V, Ti-2.5Cu, Ti-6Al-2.75Sn-4Zr-0.4Mo-0.45Si, Ti-5Al-2.5Sn, Ti-0.3Mo-0.8Ni, Ti-3Al-2.5V, Ti-6.5Al-2Zr-1Mo-1V, Ti-5.5Al-4Sn-2Zr-1Mo-1Nd-0.25Si, Ti-5.8Al-4Sn-3.5Zr-0.5Mo-0.7Nb-0.35Si-0.6C, Ti-8Al-1Mo-1V, Ti-6Al-2.75 Sn-4Zr-0.4Mo-0.45Si, Ti-5.8Al-4Sn-3.5Zr-0.5Mo-0.7Nb-0.35Si-0.6C, Ti-5Al-2Sn-4Mo-4Cr, Ti4.5Al-5Mo-2Cr-2Zr-0.2Si, Ti-6Al-2.5Mo-1.5Cr-0.5Fe-0.5Si, Ti-5Al-4.75Mo-4.75V-1Cr-1Fe, Ti-6Al-2Sn-4Zr-6Mo, Ti-6Al-2Sn-2Zr-3Mo-1Cr-2Nb-0.1Si.

Further, a base alloy of the titanium alloy is Ti-b, the Ti-b is Ti-6Al4V, the titanium alloy a is Ti-6Al4V-45Zr, the titanium alloy c is Ti-6Al4V-20Mo, the titanium alloy d is Ti-6Al4V-20Cr, and the titanium alloy e is Ti-6Al4V-20Fe.

Further, a temperature is 1000-1400° C. and a time is 48-480 h for performing the diffusion annealing treatment.

Further, a temperature is 800-1100° C. and a time is 0.5-8 h for performing the solution treatment.

Further, a temperature is 450-650° C. and a time is 2-8 h for performing the aging treatment.

Further, a temperature is 950-1050° C. and a time is 3-5 h for performing sintering for the ternary diffusion multiple A and the ternary diffusion multiple B.

Further, a distance between centers of adjacent sub-regions is 100-200 μm.

Further, after the step (8), the method further comprises: based on a raw material ratio of the titanium alloy selected to meet design requirements, weighing raw materials, performing smelting, forging and heat treatment on the raw materials, performing tensile properties test, and selecting a titanium alloy with best matching between hardness and tensile properties.

The advantages of the present disclosure over the prior art are:

Under the guidance of the pseudo spinodal decomposition theory, through the calculation of the phase diagram calculation method, the alloy composition that may have high-strength performance can be found faster and more accurately. At the same time, by using the experimental method of diffusion multiple, the relationship of "composition-microstructure-hardness" of titanium alloy can be obtained more quickly and efficiently from the experimental point of view, and the alloy composition with the highest hardness can be obtained. According to the microstructure of the alloy, it is ensured that the alloy does not produce a brittle phase during the casting process, so that the plasticity of the alloy can be controlled by heat processing and heat treatment to ensure that the titanium alloy can achieve good and strong plastic matching. By using the several high-strength titanium alloys designed by the present disclosure, a good and strong plastic matching can be achieved through testing, indicating that the alloy designed by the method of the present disclosure has a high success rate, and the method is reliable and effective.

DETAILED DESCRIPTION OF THE PRESENT DISCLOSURE

The present disclosure is further described below in connection with specific preferred embodiments, but the scope of the present disclosure is not thus limited. Ti-6Al-4V alloy is used as a base alloy.

Example 1

A method for designing a multi-component high-strength titanium alloy comprises the following steps:

According to the pseudo spinodal decomposition theory, the phase composition calculation method is used to calculate a composition range of the "Ti-6Al-4V—Cr—Mo—Fe—Zr" alloy system within which the pseudo spinodal decomposition alloy may occur, and the alloy composition of the diffusion multiple is determined.

(1) Raw materials were weighed according to a ratio, and titanium alloy ingots of five compositions of Ti6Al4V45Zr, Ti6Al4V, Ti6Al4V20Mo, Ti6Al4V20Cr and Ti6Al4V20Fe were formed after smelting;

(2) The titanium alloy ingots of the above five compositions were cut by wire cutting, specifically: two pieces of Ti6Al4V alloy with a size of 12 mm×12 mm×10 mm, two pieces of Ti6Al4V45Zr alloy with a size of 12 mm×12 mm×3 mm, one piece of each of Ti6Al4V20Cr and Ti6Al4V20Mo alloy with a size of 12 mm×12 mm×3 mm, one piece of each of Ti6Al4V20Cr, Ti6Al4V20Fe and Ti6Al4V20Mo alloy with a size of 16 mm×12 mm×3 mm; surfaces of the alloys were sanded with sandpaper, and then the surfaces were polished for later use.

Figure 1:
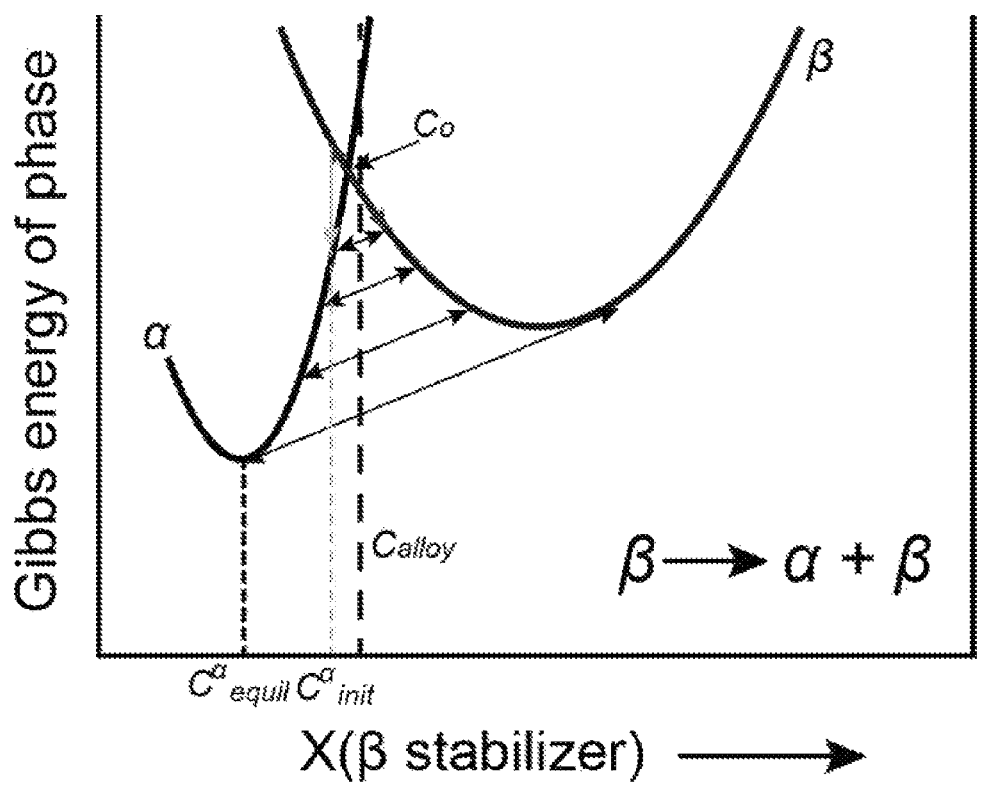
FIG. 1 shows a schematic diagram of the pseudo spinodal decomposition mechanism in prior art.
Figure 2:
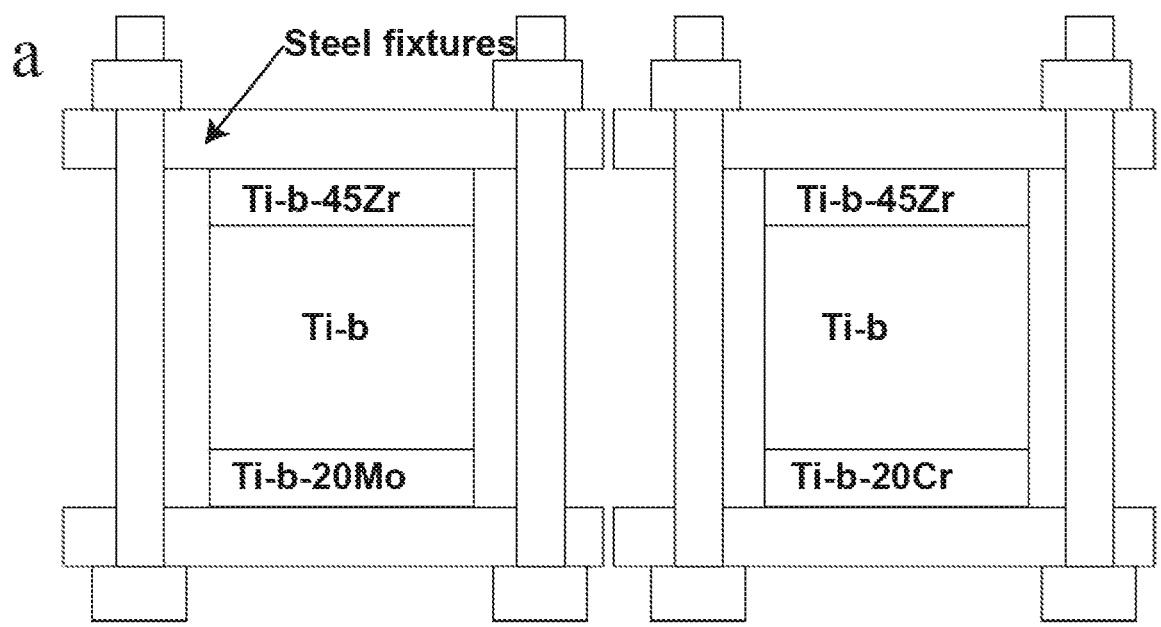
FIG. 2 is a schematic view of two ternary diffusion multiple of a first embodiment.

(3) As shown in FIG. 1, two sandwich structures Ti6Al4V45Zr—Ti6Al4V—Ti6Al4V20Mo and Ti6Al4V45Zr—Ti6Al4V—Ti6Al4V20Cr were fabricated using a steel fixture, the fixture and sample being separated by Ta foil, and then the structures were sintered for 4 hours under 1000° C. in a vacuum sintering furnace; two ternary diffusion multiple were obtained, which were labelled as ternary diffusion multiple A (Ti6Al4V45Zr—Ti6Al4V—Ti6Al4V20Mo) and ternary diffusion multiple B (Ti6Al4V45Zr—Ti6Al4V—Ti6Al4V20Cr). Then the two ternary diffusion multiple were taken out from the fixture, the surface oxide scales were grinded off and then they were polished; a multi-layer sandwich structure of Ti6Al4V45Zr— ternary diffusion multiple A-Ti6Al4V20Fe— ternary diffusion multiple-Ti6Al4V20Mo as shown in FIG. 2 was prepared with a fixture using the two diffusion multiple and the remaining three alloy blocks of step (2), and the structure was vacuum-sintered at 1000° C. for 4 hours in a vacuum sintering furnace to obtain a multi-component diffusion multiple. The multi-component diffusion multiple is taken out of the fixture, surface grinded and polished, and washed and dried using alcohol for reserve.

(4) The multi-component diffusion multiple sample was sealed in a quartz tube flushed with argon gas, and the sample was diffusion-annealed at 1200° C. for 120 hours to obtain composition gradient.

(5) The multi-component diffusion multiple was taken out from the quartz tube, solution treated, vacuum-annealed at 1050° C. for 6 hours and quenched; then the sample was wire cut from the longitudinal section to cut out two same parts, one part was spared for reserve and the other part was aging treated, vacuum-annealed at 600° C. for 6 hours and then air-cooled.

Figure 3:
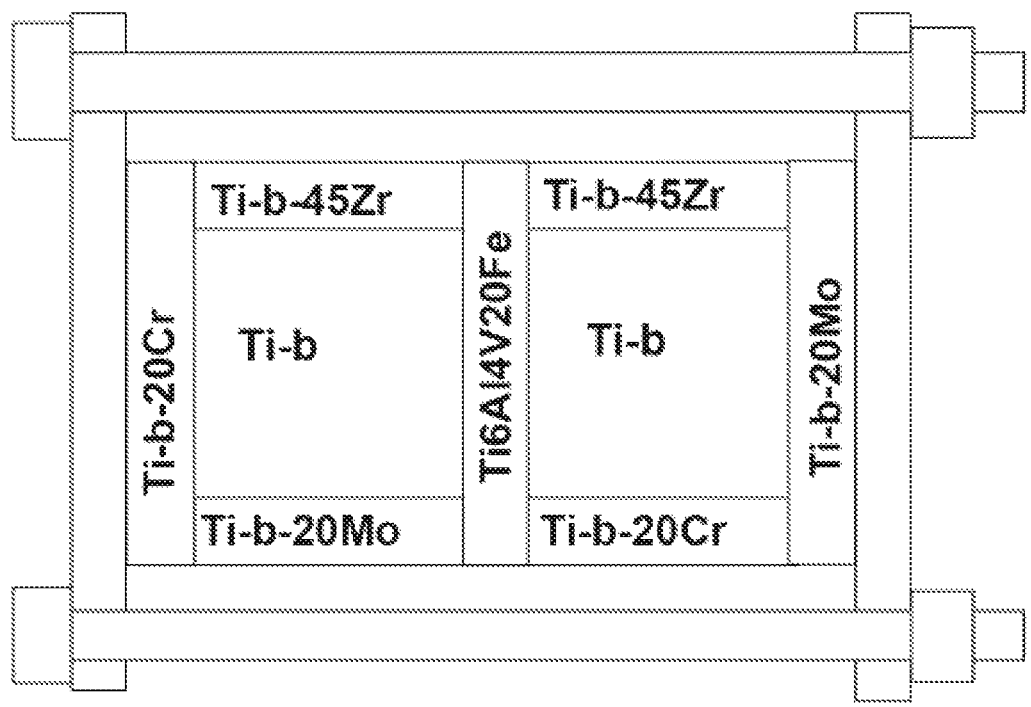
FIG. 3 is a schematic view of a multi-component diffusion multiple of the first embodiment.
Figure 4:
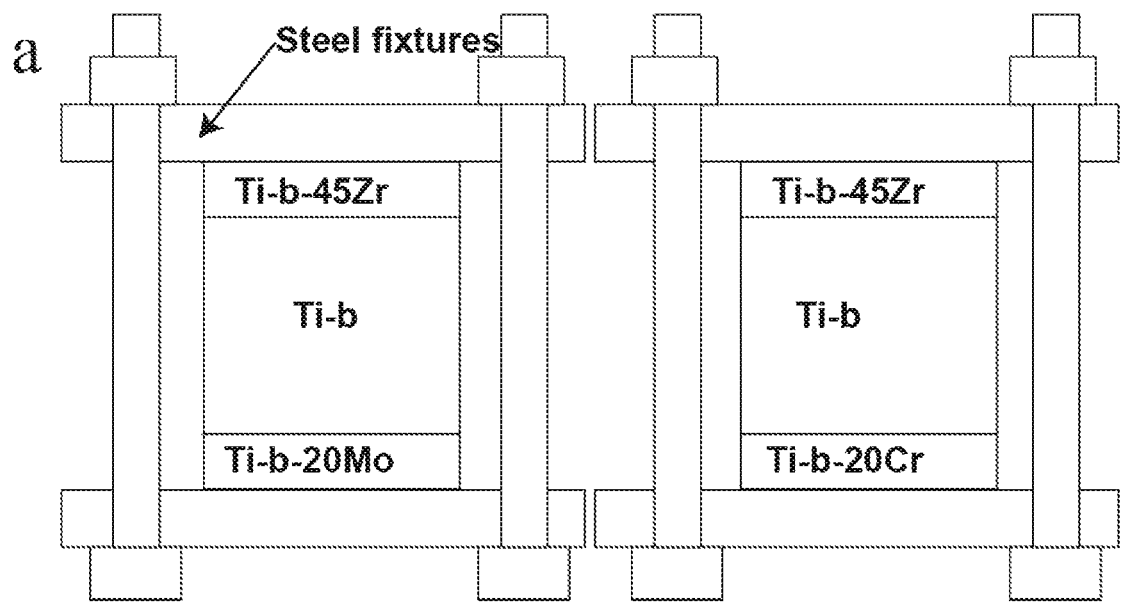
FIG. 4 is a view showing region division of composition of the multi-component diffusion couple of the first embodiment.

(6) Using microhardness or nanoindentation, in the sample diffusion area, that is, the Ti6Al4V alloy region shown in FIG. 3, was uniformly dotted, and in the ternary diffusion region, a rectangular square array was dotted, a distance between the front, back, left and right can be set to 100~200 μm; in the binary area, two rows of hardness indentation lattices were dotted. The hardness value and the location of each hardness indentation were recorded. Using an electron probe and a scanning electron microscope, the alloy composition and microstructure of each indentation area were detected and determined, and the obtained experimental data were comprehensively analyzed to establish a database of the "composition-microstructure-hardness" correspondence of the titanium alloy.

(7) According to the established database, the alloy composition corresponding to the highest hardness of the alloy was selected, its microstructure and phase composition was analyzed, and an optimal alloy composition was select.

(8) The titanium alloy designed in the step 7 was melt-cast, followed by forging and heat treatment, wherein the blank forging was performed at a temperature that is 150 to 200° C. above the α/β phase transition point of the designed alloy, and the final forging temperature was about 50° C. below the α/β phase transition point; then the alloy was solution treated and aging treated, the solution temperature was in the range of 50° C. above the α/β phase transition point to 150° C. below the α/β phase transition point, and the aging temperature was in the range of 400-650° C. After the alloy was subjected to forging and heat treatment, tensile properties were measured.

According to the database of the "composition-microstructure-hardness" correspondence of the titanium alloy according to the present embodiment, the influence of different Fe contents on the hardness of the Ti6Al4V alloy was studied. The process of selecting the optimal Ti6Al4V-xFe alloy was as follows:

The effect of Fe content on the hardness of Ti6Al4V alloy, i.e. the change rule of hardness of Ti6Al4V-xFe alloy was studied based on Ti6Al4V—Ti6Al4V20Mo—Ti6Al4V45Zr—Ti6Al4V20Cr—Ti6Al4V20Fe diffusion multiple under aging by using Ti6Al4V—Ti6Al4V20Fe diffusion couple as a targeted study system. The hardness and composition data of the alloy as shown in Table 1 was obtained by nano-indentation and electron probes:

TABLE 1

Change rule of hardness of Ti6Al4V-xFe alloy

| Diffusion distance (μm) | Al content (%) | V content (%) | Ti content (%) | Fe content (%) | Nano-indentation hardness (GPa) |
| --- | --- | --- | --- | --- | --- |
| 0 | 6.0 | 3.8 | 75.0 | 15.1 | 5.3 |
| 150 | 6.1 | 3.9 | 75.8 | 14 | 5.1 |
| 300 | 6.0 | 3.9 | 76.9 | 13.1 | 5.2 |
| 450 | 6.1 | 4.0 | 77.5 | 12.3 | 5.3 |
| 600 | 5.9 | 3.9 | 78.9 | 11.4 | 5.1 |
| 750 | 6.8 | 4.3 | 79.2 | 10.6 | 5.2 |
| 900 | 6.2 | 4.1 | 80.7 | 9.8 | 5.3 |
| 1050 | 6.3 | 4.3 | 80.9 | 9 | 5.5 |
| 1200 | 6.2 | 4.2 | 81.2 | 8.2 | 5.8 |
| 1350 | 6.5 | 4.1 | 81.8 | 7.4 | 5.7 |
| 1500 | 6.3 | 3.7 | 83.1 | 6.7 | 5.6 |
| 1650 | 6.4 | 4.0 | 83.2 | 6.3 | 5.8 |
| 1800 | 6.3 | 4.0 | 83.9 | 5.7 | 5.9 |
| 1950 | 6.4 | 3.9 | 84.2 | 5.3 | 5.9 |
| 2100 | 6.0 | 3.9 | 85.1 | 4.8 | 6.1 |
| 2250 | 6.2 | 4.3 | 84.9 | 4.5 | 6.0 |
| 2400 | 6.4 | 4.3 | 85.2 | 4 | 5.8 |
| 2550 | 6.3 | 4.1 | 86.0 | 3.445 | 5.6 |
| 2700 | 6.4 | 3.9 | 86.6 | 2.9 | 5.6 |
| 2850 | 6.3 | 4.2 | 86.6 | 2.7 | 5.3 |
| 3000 | 6.3 | 3.8 | 87.4 | 2.3 | 5.2 |
| 3150 | 6.4 | 4.5 | 87.0 | 2.013 | 4.9 |
| 3300 | 6.4 | 4.1 | 87.8 | 1.573 | 4.9 |
| 3450 | 6.4 | 4.1 | 88.0 | 1.3 | 4.9 |
| 3600 | 6.3 | 3.7 | 88.8 | 1 | 4.8 |
| 3750 | 6.5 | 4.0 | 88.8 | 0.6 | 4.7 |
| 3900 | 6.4 | 4.0 | 89.1 | 0.4 | 4.6 |
| 4050 | 6.4 | 4.1 | 89.2 | 0.2 | 4.9 |
| 4200 | 6.5 | 4.0 | 89.3 | 0.1 | 4.8 |
| 4350 | 6.4 | 4.0 | 89.5 | 0 | 4.8 |

It was found by data analysis that the alloy had the highest hardness when the Fe content was about 5%, and thus the Ti6Al4V5Fe alloy was selected as the target alloy.

The Ti6Al14V5Fe alloy was melt-cast and forged, and then forged and heat-treated. The blank forging was performed at a temperature that is 150~200° C. above the α/β phase transition point of Ti6Al4V5Fe alloy, and the final forging temperature was about 50° C. below the α/β phase transition point; then the alloy was solution treated and aging treated, the solution temperature was in the range of 50° C. above the α/β phase transition point to 150° C. below the α/β phase transition point, and the aging temperature was in the range of 400-650° C. After the alloy was subjected to forging and heat treatment, tensile properties were measured. The tensile properties of the final Ti6Al4V5Fe alloy were shown in Table 2:

TABLE 2

Performance table of Ti6Al4V5Fe alloy

| Alloy composition | Heat treatment scheme | Rm/ MPa | Rp$_{0.2}$/ Mpa | A % |
|---|---|---|---|---|
| Ti6Al4V5Fe | 700° C./0.5 h/AC + 560° C./6 h/AC | 1345 | 1265 | 8.5 |
| | 750° C./0.5 h/AC + 560° C./6 h/AC | 1280 | 1189 | 12 |
| | 820° C./0.5 h/AC + 560° C./6 h/AC | 1433 | 1317 | 4 |

The results show that the Ti6Al4V5Fe titanium alloy designed by the experimental method provided by the present disclosure can reach 1345 MPa after processing and heat treatment, and the elongation can reach 8.5%, indicating the alloy has good and strong plastic matching.

According to the database of "composition-microstructure-hardness" correspondence of titanium alloy according to the present embodiment, the influence of different Cr contents on the hardness of Ti6Al4V alloy was studied. The process of selecting the best Ti6Al4V-xCr alloy was as follows:

The effect of Cr content on the hardness of Ti6Al4V alloy, i.e. the change rule of hardness of Ti6Al4V-xCr alloy was studied based on Ti6Al4V—Ti6Al4V20Mo—Ti6Al4V45Zr—Ti6Al4V20Cr—Ti6Al4V20Fe diffusion multiple under aging by using Ti6Al4V—Ti6Al4V20Cr diffusion multiple as a targeted study system. The hardness and composition data of the alloy as shown in Table 3 was obtained by nano-indentation and electron probes:

TABLE 3

Change rule of hardness of Ti6Al4V-xCr alloy

| Diffusion distance (μm) | V content (%) | Al content (%) | Ti content (%) | Cr content (%) | Nano-indentation hardness (GPa) |
|---|---|---|---|---|---|
| 2300 | 3.9 | 5.6 | 90.4 | 0 | 4.8 |
| 2200 | 4.0 | 5.9 | 89.8 | 0.2 | 4.6 |
| 2100 | 4.2 | 6.1 | 90.1 | 0.4 | 4.8 |
| 2000 | 4.0 | 6.3 | 89.9 | 0.7 | 5.1 |
| 1900 | 4.0 | 5.8 | 88.9 | 1.1 | 5.1 |
| 1800 | 3.7 | 5.7 | 88.9 | 1.5 | 5.3 |
| 1700 | 4.0 | 6.0 | 87.9 | 1.9 | 5.4 |
| 1600 | 3.7 | 6.0 | 87.8 | 2.4 | 5.5 |
| 1500 | 3.7 | 6.1 | 87.1 | 2.9 | 5.4 |
| 1400 | 3.7 | 6.3 | 86.2 | 3.6 | 5.7 |
| 1300 | 3.5 | 6.3 | 85.6 | 4.2 | 5.7 |
| 1200 | 3.6 | 6.5 | 84.4 | 4.8 | 5.8 |
| 1100 | 3.9 | 6.6 | 83.2 | 5.6 | 5.9 |
| 1000 | 3.7 | 6.6 | 82.5 | 6.0 | 5.9 |
| 900 | 3.7 | 6.6 | 81.6 | 7.2 | 5.4 |
| 800 | 3.5 | 6.5 | 81.1 | 7.8 | 5.0 |
| 700 | 3.9 | 6.6 | 79.6 | 9.2 | 5.2 |
| 600 | 3.8 | 6.5 | 78.9 | 10.4 | 4.7 |
| 500 | 3.8 | 6.5 | 77.8 | 11.4 | 4.9 |
| 400 | 3.6 | 6.4 | 77.1 | 12.6 | 5.2 |
| 300 | 3.7 | 6.4 | 75.7 | 13.5 | 4.6 |
| 200 | 3.8 | 6.5 | 74.3 | 15 | 4.8 |
| 100 | 3.6 | 6.4 | 73.2 | 16.7 | 4.2 |
| 0 | 3.7 | 6.3 | 74.2 | 18.2 | 4.2 |

It was found by data analysis that the alloy had the highest hardness when the Cr content was about 6%, and thus the Ti6Al4V6Cr alloy was selected as the target alloy.

The Ti6Al4V6Cr alloy was melt-cast and forged, and then forged and heat-treated. The blank forging was performed at a temperature that is 150~200° C. above the α/β phase transition point of Ti6Al4V6Cr alloy, and the final forging temperature was about 50° C. below the α/β phase transition point; then the alloy was solution treated and aging treated, the solution temperature was in the range of 50° C. above the α/β phase transition point to 150° C. below the α/β phase transition point, and the aging temperature was in the range of 400-650° C. After the alloy was subjected to forging and heat treatment, tensile properties were measured. The tensile properties of the final Ti6Al4V6Cr alloy were shown in Table 4:

TABLE 4

Performance table of Ti6Al4V6Cr alloy

| Alloy composition | Heat treatment scheme | Rm/ MPa | Rp$_{0.2}$/ Mpa | A % |
|---|---|---|---|---|
| Ti6Al4V6Cr | 740° C./0.5 h/AC + 500° C./6 h/AC | 1329 | 1287 | 7.6 |
| | 790° C./0.5 h/AC + 500° C./6 h/AC | 1560 | 1477 | 3.2 |
| | 790° C./0.5 h/AC + 650° C./6 h/AC | 1153 | 1106 | 13.1 |

The results show that the Ti6Al4V6Cr titanium alloy designed by the experimental method provided by the present disclosure can reach 1329 MPa after processing and heat treatment, and the elongation can reach 7.6%, indicating the alloy has good and strong plastic matching.

According to the database of "composition-microstructure-hardness" correspondence of titanium alloy according to the present embodiment, the influence of different Mo contents on the hardness of Ti6Al4V alloy was studied. The process of selecting the best Ti6Al4V-xMo alloy was as follows:

The effect of Mo content on the hardness of Ti6Al4V alloy, i.e. the change rule of hardness of Ti6Al4V-xMo alloy was studied based on Ti6Al4V—Ti6Al4V20Mo—Ti6Al4V45Zr—Ti6Al4V20Cr—Ti6Al4V20Fe diffusion multiple under aging by using Ti6Al4V—Ti6Al4V20Mo diffusion couple as a targeted study system. The hardness and composition data of the alloy as shown in Table 5 was obtained by microhardness and electron probes:

TABLE 5

Change rule of hardness of Ti6Al4V-xMo alloy

| Diffusion distance (μm) | Mo content (%) | Al content (%) | Ti content (%) | V content (%) | Microhardness (MPa) |
|---|---|---|---|---|---|
| 0 | 21 | 5.0 | 68.7 | 4.665 | 350.4 |
| 80 | 19.5 | 5.1 | 70.0 | 4.750 | 350.5 |
| 160 | 17.7 | 5.4 | 72.4 | 5.027 | 370.2 |
| 240 | 15.3 | 5.5 | 74.1 | 4.980 | 452.3 |
| 320 | 13.6 | 5.6 | 75.7 | 5.046 | 507.8 |
| 400 | 11.9 | 5.7 | 76.8 | 5.101 | 534.3 |
| 480 | 10.2 | 5.8 | 78.5 | 5.376 | 524.4 |
| 560 | 8.7 | 5.9 | 80.2 | 5.105 | 551.4 |
| 640 | 7.7 | 6.1 | 80.6 | 5.391 | 565.3 |
| 720 | 6.4 | 6.2 | 81.5 | 5.4 | 570.4 |
| 800 | 5.7 | 6.2 | 82.7 | 5.5 | 597 |
| 880 | 4.7 | 6.3 | 83.7 | 5.3 | 588.6 |
| 960 | 4.1 | 6.2 | 84.0 | 5.4 | 574.2 |
| 1040 | 4.1 | 6.3 | 84.0 | 5.4 | 545.1 |
| 1120 | 2.8 | 5.8 | 83.0 | 5.2 | 498.1 |
| 1200 | 2.8 | 6.3 | 85.5 | 5.2 | 494.4 |
| 1280 | 1.9 | 6.4 | 86.1 | 5.3 | 502.9 |
| 1360 | 1.8 | 6.5 | 86.4 | 5.1 | 477.9 |
| 1440 | 1.6 | 6.6 | 86.8 | 4.8 | 497 |
| 1520 | 1.5 | 6.5 | 86.3 | 5.5 | 457.2 |
| 1600 | 1.3 | 7.1 | 88.0 | 5.0 | 464.3 |
| 1680 | 1.0 | 6.6 | 86.7 | 5.5 | 477 |
| 1760 | 1.2 | 6.4 | 86.7 | 5.4 | 445.3 |

TABLE 5-continued

Change rule of hardness of Ti6Al4V-xMo alloy

| Diffusion distance (μm) | Mo content (%) | Al content (%) | Ti content (%) | V content (%) | Microhardness (MPa) |
|---|---|---|---|---|---|
| 1840 | 0.9 | 6.3 | 86.6 | 5.3 | 437.8 |
| 1920 | 0.6 | 6.6 | 87.4 | 5.0 | 446 |
| 2000 | 0.5 | 6.5 | 87.5 | 5.3 | 455.6 |
| 2080 | 0.3 | 6.3 | 87.3 | 5.8 | 474.4 |
| 2160 | 0.1 | 6.4 | 87.7 | 5.2 | 476.4 |

It was found by data analysis that the alloy had the highest hardness when the Mo content was about 6%, and thus the Ti6Al4V6 Mo alloy was selected as the target alloy.

The Ti6Al4V6 Mo alloy was melt-cast and forged, and then forged and heat-treated. The blank forging was performed at a temperature that is 150~200° C. above the α/β phase transition point of Ti6Al4V6 Mo alloy, and the final forging temperature was about 50° C. below the α/β phase transition point; then the alloy was solution treated and aging treated, the solution temperature was in the range of 50° C. above the α/β phase transition point to 150° C. below the α/β phase transition point, and the aging temperature was in the range of 400-650° C. After the alloy was subjected to forging and heat treatment, tensile properties were measured. The tensile properties of the final Ti6Al4V6 Mo alloy were shown in Table 6:

TABLE 6

Performance table of Ti6Al4V6Mo alloy

| Alloy composition | Heat treatment scheme | Rm/ MPa | Rp$_{0.2}$/ Mpa | A % |
|---|---|---|---|---|
| Ti6Al4V6Cr | 835° C./0.5 h/AC + 500° C./6 h/AC | 1543 | 1456 | 4.8 |
| | 830° C./0.5 h/AC + 530° C./6 h/AC | 1417 | 1345 | 6.4 |
| | 700° C./0.5 h/AC + 500° C./6 h/AC | 1228 | 1174 | 10.8 |

The results show that the Ti6Al4V6Mo titanium alloy designed by the experimental method provided by the present disclosure can reach 1417 MPa after processing and heat treatment, and the elongation can reach 6.4%, indicating the alloy has good and strong plastic matching.

The above results show that the three titanium alloys designed by this method can obtain good and strong plastic matching. The present disclosure utilizes the experimental method of diffusion multiple to carry out the composition design of the multi-component high-strength titanium alloy material. Through the material design method, the correspondence of the alloy composition-microstructure-performance can be obtained quickly and accurately, then the alloy design is targeted, and an optimal alloy composition is obtained; and it is fast and efficient, saves time and effort and has strong practical value. The above three high-strength titanium alloys designed by the method can obtain good comprehensive performance, indicating that the method is effective and reliable. Compared with the traditional alloying method, the material design method is more objective, shortens the test period and accelerates the alloy design process.

The above description is only preferred embodiments of the present application, and is not intended to limit the scope of the application. Although the present application is disclosed in the preferred embodiments, it is not limited thereto. Rather, for one skilled in the art, without departing from the scope of the technical solution of the present disclosure, a slight change or modification made based on the technical content disclosed above is equivalent to the corresponding embodiment and is within the technical scope of the present application.

What is claimed is:

1. A method for designing multi-component high-strength titanium alloy, comprising the following steps:
   (1) weighing respectively, titanium alloy raw materials—titanium alloy a Ti-b-45Zr, titanium alloy f Ti-b, titanium alloy c Ti-b-20Mo, titanium alloy d Ti-b-20Cr, and titanium alloy e Ti-b-20Fe, recording a raw material ratio of the titanium alloys, and smelting and forming the titanium alloy raw materials into five titanium alloy ingots;
   (2) cutting respectively, the five titanium alloy ingots obtained in step (1) into cubes, the cubes comprising a titanium alloy a cube, a titanium alloy f cube, a titanium alloy c cube, a titanium alloy d cube, and a titanium alloy e cube;
   (3) stacking and fixing the cubes obtained in step (2) sequentially in the order of the titanium alloy a cube, the titanium alloy f cube and the titanium alloy c cube, and sintering them to form a ternary diffusion multiple A;
   stacking and fixing the cubes obtained in step (2) sequentially in the order of the titanium alloy a cube, the titanium alloy f cube and the titanium alloy d cube, and sintering them to form a ternary diffusion multiple B;
   (4) stacking and fixing the titanium alloy d, c and e cubes as well as the ternary diffusion multiple A and the ternary diffusion multiple B obtained in step (3) in the order of the titanium alloy d cube, the ternary diffusion multiple A, the titanium alloy e cube, the ternary diffusion multiple B and the titanium alloy c cube in a length direction, and sintering them to form a multi-component diffusion multiple; in the multi-component diffusion multiple, the ternary diffusion multiple A comprises titanium alloy a, titanium alloy f and titanium alloy c from bottom to top in a height direction, and the ternary diffusion multiple B comprises titanium alloy a, titanium alloy f and titanium alloy d from bottom to top in a height direction;
   (5) performing diffusion annealing treatment on the multi-component diffusion multiple obtained in step (4) to obtain composition gradient;
   (6) performing solution treatment and aging treatment on the multi-component diffusion multiple obtained in step (5);
   (7) grinding and polishing the surface of the sample to perform microstructure and hardness testing on a gradient region, and establishing a titanium alloy table based on the microstructure and hardness testing, wherein the titanium alloy table comprises a correspondence between composition, microstructure, and hardness for elements comprising Fe, Mo and Cr;
   (8) selecting and determining a titanium alloy which has highest hardness according to the titanium alloy table obtained in step (7);
   (9) melt-casting, forging the selected titanium alloy for a first time; and
   (10) forging the selected titanium alloy for a second time, and heat-treating the selected titanium alloy, and performing a tensile properties test to the selected titanium alloy, and wherein:
   a base alloy of the titanium alloy is Ti-b; the base alloy comprises an α-type titanium alloy and an α-β-type titanium alloy, and wherein the α-type titanium alloy and the α-β-type titanium alloy comprise: Ti-6Al-4V, Ti-3Al-2.5V, Ti-2.5Cu, Ti-6Al-2.75Sn-4Zr-0.4Mo-0.45Si, Ti-5Al-2.5Sn, Ti-0.3Mo-0.8Ni, Ti-3Al-2.5V, Ti-6.5Al-2Zr-1Mo-1V, Ti-5.5Al-4Sn-2Zr-1Mo-1Nd-0.25Si, Ti-5.8Al-4Sn-3.5Zr-0.5Mo-0.7Nb-0.35Si-0.6C, Ti-8Al-1Mo-1V, Ti-6Al-2.75Sn-4Zr-0.4Mo-0.45Si, Ti-5.8Al-4Sn-3.5Zr-0.5Mo-0.7Nb-0.35Si-0.6C, Ti-5Al-2Sn-4Mo-4Cr, Ti4.5Al-5Mo-2Cr-2Zr-0.2Si, Ti-6Al-2.5Mo-1.5Cr-0.5Fe-0.3Si, Ti-6.5Al-1.5Zr-3.5Mo-0.3Si, Ti-5Al-4.75Mo-4.75V-1Cr-1Fe, Ti-6Al-2Sn-4Zr-6Mo, Ti-6Al-2Sn-2Zr-3Mo-1Cr-2Nb-0.1Si.

2. The method according to claim 1, wherein a base alloy of the titanium alloy is Ti-b, the Ti-b is Ti-6Al4V, the titanium alloy a is Ti-6Al4V-45Zr, the titanium alloy c is Ti-6Al4V-20Mo, the titanium alloy d is Ti-6Al4V-20Cr, and the titanium alloy e is Ti-6Al4V-20Fe.

3. The method according to claim 2, wherein a temperature is 1000-1400° C. and a time is 48-480 h for performing the diffusion annealing treatment.

4. The method according to claim 3, wherein a temperature is 800-1100° C. and a time is 0.5-8 h for performing the solution treatment.

5. The method according to claim 4, wherein a temperature is 450-650° C. and a time is 2-8 h for performing the aging treatment.

6. The method according to claim 5, wherein a temperature is 950-1050° C. and a time is 3-5 h for performing sintering for the ternary diffusion multiple A and the ternary diffusion multiple B.

7. The method according to claim 1, wherein a distance between geometric center points of adjacent sub-regions is 100-200 μm.

* * * * *